United States Patent
Gödiker et al.

(10) Patent No.: US 12,370,029 B2
(45) Date of Patent: Jul. 29, 2025

(54) ZIRCONIUM DIOXIDE GREEN BODY WITH COLOR AND TRANSLUCENCY GRADIENTS

(71) Applicant: Vita Zahnfabrik H. Rauter GmbH & Co. KG, Bad Säckingen (DE)

(72) Inventors: Michael Gödiker, Bad Säkingen (DE); Eva Kolb, Bad Säkingen (DE); Christian Strasser, Bad Säkingen (DE)

(73) Assignee: Vita Zahnfabrik H. Rauter GmbH & Co. KG, Bad Säkingen (DE)

( * ) Notice: Subject to any disclaimer, the term of this patent is extended or adjusted under 35 U.S.C. 154(b) by 551 days.

(21) Appl. No.: 17/632,539

(22) PCT Filed: Aug. 5, 2020

(86) PCT No.: PCT/EP2020/072048
§ 371 (c)(1),
(2) Date: Feb. 3, 2022

(87) PCT Pub. No.: WO2021/023791
PCT Pub. Date: Feb. 11, 2021

(65) Prior Publication Data
US 2022/0273403 A1    Sep. 1, 2022

(30) Foreign Application Priority Data

Aug. 8, 2019  (EP) .................................... 19190774
Aug. 8, 2019  (EP) .................................... 19190778

(51) Int. Cl.
A61C 13/00   (2006.01)
A61K 6/818   (2020.01)
(Continued)

(52) U.S. Cl.
CPC .......... *A61C 13/0022* (2013.01); *A61K 6/818* (2020.01); *A61K 6/822* (2020.01);
(Continued)

(58) Field of Classification Search
None
See application file for complete search history.

(56) References Cited

U.S. PATENT DOCUMENTS 9,687,325 B2   6/2017   Park et al.
10,231,807 B2  3/2019   Yamada et al.
(Continued)

FOREIGN PATENT DOCUMENTS

CN    102 285 795 A    12/2011
CN    103 058 665 B    4/2013
(Continued)

OTHER PUBLICATIONS

Machine translation of CN 102285795, retrieved from EPO database Oct. 30, 2024 (Year: 2024).*
(Continued)

*Primary Examiner* — Timothy Kennedy
(74) *Attorney, Agent, or Firm* — Dority & Manning, P.A.

(57) ABSTRACT

The invention relates to a sintered molding with a color gradient for use in the manufacture of dental restorations, obtainable by sintering a compression-molded element comprising five or more different ceramic powder layers, each powder layer comprising at least two different base powders and each base powder containing at least 80 wt. % $ZrO_2$, each weight amount being relative to the total weight of the base powder.

19 Claims, 1 Drawing Sheet

Layering (25 : 15 : 20 : 15 : 25)

(51) Int. Cl.
  *A61K 6/822* (2020.01)
  *A61K 6/824* (2020.01)
  *B28B 1/00* (2006.01)
  *B28B 3/00* (2006.01)
  *B28B 3/02* (2006.01)
  *B28B 11/24* (2006.01)
  *C04B 35/488* (2006.01)
  *C04B 35/64* (2006.01)
  *C04B 35/645* (2006.01)

(52) U.S. Cl.
  CPC .............. *A61K 6/824* (2020.01); *B28B 1/008* (2013.01); *B28B 3/003* (2013.01); *B28B 3/02* (2013.01); *B28B 11/243* (2013.01); *C04B 35/4885* (2013.01); *C04B 35/64* (2013.01); *C04B 35/6455* (2013.01); *A61C 2201/002* (2013.01); *C04B 2235/3217* (2013.01); *C04B 2235/3224* (2013.01); *C04B 2235/3225* (2013.01); *C04B 2235/3244* (2013.01); *C04B 2235/3272* (2013.01); *C04B 2235/3277* (2013.01); *C04B 2235/5436* (2013.01); *C04B 2235/5445* (2013.01); *C04B 2235/604* (2013.01); *C04B 2235/608* (2013.01); *C04B 2235/75* (2013.01); *C04B 2235/77* (2013.01); *C04B 2235/786* (2013.01); *C04B 2235/9661* (2013.01)

(56) References Cited

U.S. PATENT DOCUMENTS

| | | | |
|---|---|---|---|
| 10,391,671 B2 | 8/2019 | Tholey et al. | |
| 10,441,391 B2 | 10/2019 | Volkl et al. | |
| 11,034,051 B2 | 6/2021 | Tholey et al. | |
| 2008/0118894 A1* | 5/2008 | Rothbrust | C04B 41/4537 428/688 |
| 2008/0303181 A1* | 12/2008 | Holand | C04B 35/6264 264/16 |
| 2015/0282905 A1* | 10/2015 | Jahns | C04B 35/6263 433/167 |
| 2016/0157971 A1 | 6/2016 | Rothbrust et al. | |
| 2017/0273764 A1 | 9/2017 | Volkl et al. | |
| 2018/0125616 A1* | 5/2018 | Kitamura | C04B 35/486 |
| 2018/0327319 A1 | 11/2018 | Li et al. | |
| 2019/0099245 A1 | 4/2019 | Rothbrust et al. | |
| 2019/0231494 A1* | 8/2019 | Dittmann | A61C 13/0022 |

FOREIGN PATENT DOCUMENTS

| | | |
|---|---|---|
| CN | 104844200 A | 8/2015 |
| EP | 2 829 251 A1 | 1/2015 |
| EP | 2 965 713 A1 | 1/2016 |
| EP | 2 995 434 A1 | 3/2016 |
| EP | 3 400 929 A1 | 11/2018 |
| JP | 2017185163 A | 10/2017 |
| KR | 101 324 467 B1 | 11/2013 |
| KR | 101601948 B1 | 3/2016 |
| WO | WO 2013/156483 A1 | 10/2013 |

OTHER PUBLICATIONS

Machine translation of KR 101601948, retrieved from EPO database Oct. 30, 2024 (Year: 2024).*

International Search Report for PCT/EP2020/072048, dated Nov. 2, 2020, 8 pages.

* cited by examiner

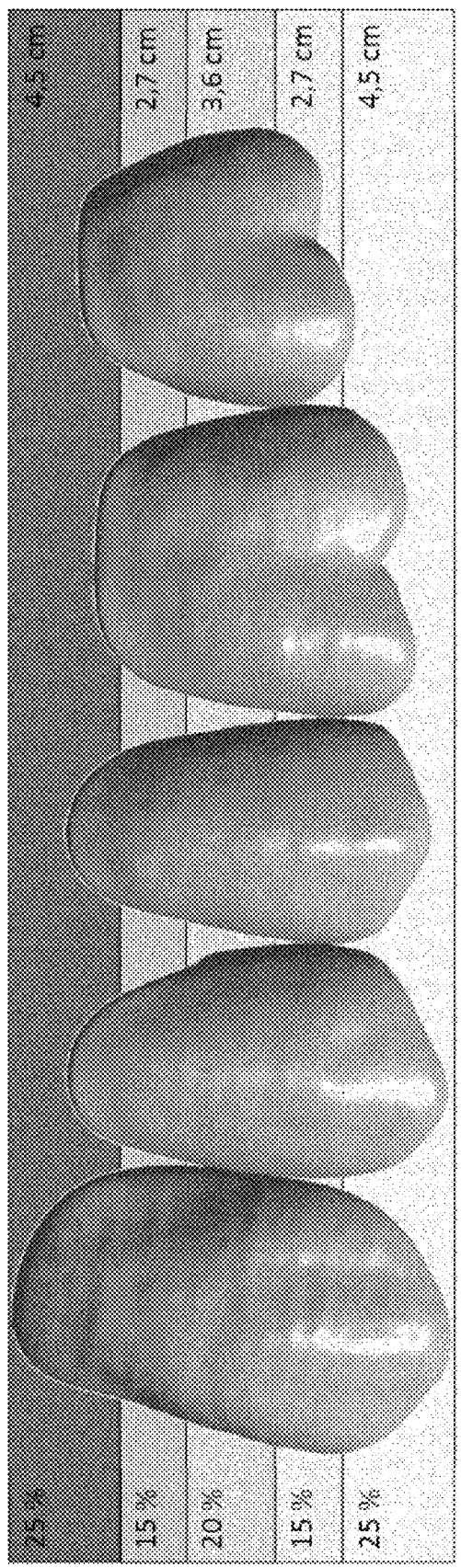

ZIRCONIUM DIOXIDE GREEN BODY WITH COLOR AND TRANSLUCENCY GRADIENTS

CROSS REFERENCE TO RELATED APPLICATIONS

This application is the national stage entry of International Patent Application No. PCT/EP2020/072048 having a filing date of Aug. 5, 2020, which claims priority to and the benefit of European Patent Application No. 19190774.0 filed in the European Patent Office on Aug. 8, 2019 and European Patent Application No. 19190778.1 filed in the European Patent Office on Aug. 8, 2019, the entire contents of which are incorporated herein by reference.

The present invention relates to a sintered molding with a color gradient for use in the preparation of dental restorations, and the use of the sintered molding for dental restorations.

Both a wide variety of organic polymer materials and ceramic materials are known for dental restorations. Ceramic materials usually have a higher strength, but are more difficult to process for dental restorations when it comes to the tailor-made production thereof. For ceramic dental restorations, both glass-ceramic and oxide-ceramic materials have become established on the market. For the preparation of dental restorations based on glass ceramics, melting processes are usually employed, while powder-technological pressing and sintering methods are required for oxide-ceramic materials.

In the prior art, multilayered blocks for dental CAD-CAM applications made of feldspar or leucite ceramics have been known. These correspond to the appearance of natural teeth under aesthetic aspects, but usually have a strength within a range of from 150 to 200 MPa. However, such strengths are less suitable, especially for dental restorations having a thin wall thickness. On the other hand, high strengths can be achieved with layered zirconia blocks. However, these are usually too opaque to be employed as a monolithic dental restoration. Thus, the use of high strength zirconia restorations requires manual reworking. This may involve infiltrating the porous scaffolds with colored liquids already before sintering, or color-matching the sintered restorations individually to the natural tooth color using stains or veneering ceramics.

A particular challenge with dental restorations is to produce a naturally appearing color gradient in the ceramic restoration. At the same time, high demands are placed on dental restorations with respect to their strength, especially their edge strength, translucency, and processability.

Surprisingly, it has been found that the problems indicated in the prior art can be solved by the present invention. In particular, it has been found that a system comprising only a few base powders can be used to produce a gradual color gradient in ceramic moldings in which both the translucency and the strength of the final product can be individually adjusted.

In a first aspect, the present invention relates to a sintered molding with a color gradient for use in the preparation of dental restorations, obtainable by sintering a compression molding comprising five or more different ceramic powder layers, wherein each powder layer comprises at least two different base powders, and said base powders each have at least 80% by weight of zirconia ($ZrO_2$), the indicated weight being based on the total weight of the base powder.

Within the scope of the present invention, a ceramic powder layer consists of at least two distinguishable base powders, preferably three or four distinguishable base powders, wherein the ceramic powder layer is preferably in the form of a homogeneous mixture of the base powders. The ceramic powder layers are preferably stacked in layers, wherein the respectively neighboring powder layers differ in their chemical compositions and/or physical properties. The differences in the compositions of the individual powder layers can be achieved by the kinds and amounts of selected suitable base powders. Therefore, the ceramic powder layers comprise at least two different base powders. In one embodiment, at least two, preferably at least three and especially all ceramic powder layers comprise the same base powders, but in different amounts. It has been found that a modular system can be constructed with a limited number of suitable base powders, by means of which the properties, especially the color, the translucency and physical properties of each individual ceramic powder layer, can be adjusted. In addition to the ceramic components, the ceramic powder layers usually include organic components, such as pressing additives. However, the proportion thereof, if any, is limited and should not exceed 10% by weight, based on the ceramic powder layer.

In a preferred embodiment, one or more of the ceramic powder layers, especially each ceramic powder layer, preferably includes at least three base powders, preferably four base powders. In particular, sintering a compression molding comprising five or more different ceramic powder layers employed according to the invention shows particular advantages. Especially with five or more than five ceramic powder layers, a good color gradient and property gradient can be achieved, which is important for dental restorations. Thus, in particular, the artificial tooth necks, which are designed in deeper and darker colors, can be adjusted in a gradual transition to the lighter cutting and dentin regions of artificial teeth, thus taking the aesthetic and mechanical demands into account.

In a specifically preferred embodiment, the sintered moldings according to the invention have five powder layers, wherein each powder layer has four different base powders, but wherein each powder layer has different amounts of the respective base powders. Surprisingly, it has been found that operation may be particularly effective and inexpensive if each ceramic powder layer has four or more base powders. Therefore, the present invention further relates to a ceramic powder layer comprising four or more base powders.

The base powders to be employed according to the invention each comprise at least 80% by weight zirconia ($ZrO_2$), and preferably at least 0.02% by weight $Al_2O_3$, the indicated weights being respectively based on the total weight of the components of the base powder.

In a preferred embodiment of the present invention, each ceramic powder layer of the compressed molding has one or more coloring metal oxides. In another embodiment, the concentration of the coloring metal oxides is different in each powder layer. Preferably, each intermediate layer, i.e. each powder layer bounded by two directly neighboring powder layers (neighboring layers), is surrounded by a neighboring layer that has a higher concentration of coloring metal oxides as compared to the intermediate layer. Preferably, each intermediate layer is surrounded by a neighboring layer that has a lower concentration of coloring metal oxides. More preferably, each intermediate layer is surrounded by one neighboring layer that has a lower concentration of coloring metal oxides, and one neighboring layer that has a higher concentration of coloring metal oxides.

In a preferred embodiment of the invention, the compressed molding has powder layers in which, proceeding from an outer powder layer, the concentration of one or more coloring metal oxides increases from layer to layer. In particular, this has the advantage that a gradual color gradient can be created. In another preferred embodiment of the invention, one or more of the ceramic powder layers of the compressed molding, preferably all powder layers, have coloring metal oxides in an amount of from 0.1 to 2.5% by weight, more preferably from 0.2 to 2.2% by weight, and especially from 0.2 to 1.5% by weight, respectively based on the total weight of the powder layer.

In a preferred embodiment, the compressed molding has powder layers in which, proceeding from an outer powder layer, the concentration of at least one coloring metal oxide increases from layer to layer, preferably all the way to the opposite outer layer.

In a preferred embodiment of the present invention, each ceramic powder layer of the compressed molding includes $Fe_2O_3$. In another embodiment, the concentration of $Fe_2O_3$ is different in each powder layer. Preferably, each intermediate layer, i.e. each powder layer bounded by two directly neighboring powder layers (neighboring layers), is surrounded by one neighboring layer that has a higher concentration of $Fe_2O_3$ as compared to the intermediate layer. Preferably, each intermediate layer is surrounded by one neighboring layer that has a lower concentration of $Fe_2O_3$. More preferably, each intermediate layer is surrounded by one neighboring layer that has a lower concentration of $Fe_2O_3$, and one neighboring layer that has a higher concentration of $Fe_2O_3$.

In a preferred embodiment of the invention, the compressed molding has powder layers in which, proceeding from an outer powder layer, the concentration of $Fe_2O_3$ increases from layer to layer. In particular, this has the advantage that a gradual color gradient can be created. In another preferred embodiment of the invention, one or more of the ceramic powder layers of the compressed molding, preferably all powder layers, include $Fe_2O_3$ in an amount of from 0.01 to 0.25% by weight, more preferably from 0.02 to 0.2% by weight, and especially from 0.1 to 0.18% by weight, respectively based on the total weight of the powder layer.

In a preferred embodiment of the present invention, each ceramic powder layer of the compressed molding includes $Er_2O_3$. In another embodiment, the concentration of $Er_2O_3$ is different in each powder layer. Preferably, each intermediate layer, i.e. each powder layer bounded by two directly neighboring powder layers (neighboring layers), is surrounded by one neighboring layer that has a higher concentration of $Er_2O_3$ as compared to the intermediate layer. Preferably, each intermediate layer is surrounded by one neighboring layer that has a lower concentration of $Er_2O_3$. More preferably, each intermediate layer is surrounded by one neighboring layer that has a lower concentration of $Er_2O_3$, and one neighboring layer that has a higher concentration of $Er_2O_3$.

In a preferred embodiment of the invention, the compressed molding has powder layers in which, proceeding from an outer powder layer, the concentration of $Er_2O_3$ increases from layer to layer. In particular, this has the advantage that a gradual color gradient can be created. In another preferred embodiment of the invention, one or more of the ceramic powder layers of the compressed molding, preferably all powder layers, include $Er_2O_3$ in an amount of from 0.01 to 1.5% by weight, more preferably from 0.05 to 1.2% by weight, and especially from 0.1 to 0.9% by weight, or from 0.2 to 0.5% by weight, respectively based on the total weight of the powder layer.

In another preferred embodiment, one or more of the powder layers preferably each powder layer, of the compressed molding has $Co_3O_4$. Usually, the amount of $Co_3O_4$ may be within a range of from 0.001 to 0.01, more preferably from 0.002 to 0.08% by weight, and especially from 0.003 to 0.006% by weight, respectively based on the total weight of the powder layer.

The base powders are suitable for preparing dental restorations, and therefore meet the necessary requirements of biocompatibility even in a sintered state. The high proportion of zirconia, which is preferably stabilized by yttria, additionally provides a high strength of the finally sintered ceramics. The base powders are selected so that they are matched to one another in terms of grain sizes and sintering behavior, so that sintering voids do not occur upon sintering. The mixing of the base powders can achieve individual coloring and translucency in each ceramic powder layer, which is in turn selected to result in a continuous and gradual color gradient with the adjacent powder layers, if any.

In a preferred embodiment of the present invention, the base powders include $Al_2O_3$ in an amount of from 0.02 to 0.6% by weight, more preferably from 0.03 to 0.4% by weight, and especially from 0.04 to 0.3% by weight, preferably from 0.04 to 0.2% by weight, or from 0.03 to 0.1%, or especially from 0.02 to 0.08% by weight, respectively based on the total weight of the base powders.

The presence of yttria or erbium oxide is advantageous for phase stabilization of the zirconia-based ceramics in the sintered state.

In a preferred embodiment, at least one, preferably at least two or three, of the base powders, especially all the base powders, comprise yttria ($Y_2O_3$) and/or erbium oxide ($Er_2O_3$), preferably in an amount of at least 3% by weight, especially at least 5% by weight, or at least 6% by weight, and especially from 3.0 to 11% by weight, especially from 5 to 10% by weight, preferably from 4.5 to 11% by weight, especially from 6 to 10% by weight, respectively based on the total weight of the components of the base powder.

In an embodiment of the present invention, at least one of the base powders, preferably at least two or at least three, of the base powders include coloring metal oxides. For example, these coloring metal oxides may be selected from the group consisting of Iron oxide ($Fe_2O_3$), cobalt oxide ($Co_3O_4$), and erbium oxide ($Er_2O_3$). Individual tooth colors can be created by adding these coloring metal oxides. A defined balanced material can be obtained by mixing several base powders in each ceramic powder layer.

In an embodiment of the present invention, at least one of the base powders, preferably at least two or at least three of the base powders, include zirconia, optionally together with hafnia, in an amount of at least 89% by weight, preferably in an amount of from 89 to 98% by weight, especially from 90 to 96% by weight, respectively based on the total weight of the components of the base powder.

In one embodiment, the base powders may include zirconia and hafnia, preferably in a weight ratio of $ZrO_2$ to $HfO_2$ of 25:1 to 98:1, especially from 30:1 to 90:1, and especially from 50:1 to 90:1.

In a preferred embodiment, the powder layers include a base powder A, which contains from 92 to 96% by weight zirconia, from 0.02 to 0.4% by weight, preferably from 0.02 to 0.1% by weight, alumina, from 3.5 to 6.5% by weight, or from 5.0 to 10% by weight, preferably from 5.0 to 9.5% by weight, yttria, and from 0.02 to 0.1% by weight cobalt oxide, the indicated weights being respectively based on the total weight of base powder A.

In another preferred embodiment, the powder layers include a base powder B, which contains from 85 to 93% by weight zirconia, from 0.02 to 0.4% by weight, preferably from 0.02 to 0.1% by weight, alumina, and from 7.5 to 11% by weight erbium oxide, the indicated weights being respectively based on the total weight of base powder B.

In another embodiment, the powder layers include a base powder C, which contains from 90 to 94% by weight zirconia, from 0.02 to 0.4% by weight, preferably from 0.02 to 0.1% by weight, alumina, and from 5.5 to 8.0% by weight, or from 6.5 to 10% by weight, preferably from 6.5 to 9.5% by weight, yttria, the indicated weights being respectively based on the total weight of base powder C.

In another preferred embodiment of the present invention, the powder layers include a base powder D, which contains from 90 to 94% by weight zirconia, from 0.02 to 0.4% by weight, preferably from 0.02 to 0.1% by weight, alumina, from 5.5 to 8.0% by weight, or from 6.5 to 10% by weight, preferably from 6.5 to 9.5% by weight, yttria, and from 0.1 to 0.3% by weight iron oxide, the indicated weights being respectively based on the total weight of base powder D.

In another embodiment of the present invention, at least one base powder, preferably all base powders, additionally include organic components, preferably in an amount of from 3 to 6% by weight, especially in an amount of from 4 to 5% by weight. Suitable organic components include, in particular, binders and pressing additives, which can be easily removed thermally in a debinding step. Suitable binders for zirconia sintered powders are known to those skilled in the art. These include, for example, polyvinyl alcohol (PVA).

Preferably, the base powders have a bulk density of below 1.2 g/cm$^3$.

It has proven advantageous to employ base powders having an average grain size $D_{50}$ of from 35 µm to 85 µm, preferably from 40 µm to 80 µm, and especially from 50 µm to 70 µm, or from 40 to 60 µm. The granular powders are measured dry by laser diffraction using a Cilas granulometer.

Usually, the inorganic components of the base powders, i.e., after removing the organic components, such as binders etc., have a particle size $D_{50}$ of from 0.1 to 1 µm, preferably from 0.2 µm to 0.8 µm, and especially from 0.2 µm to 0.7 µm, as measured by laser diffraction. It has been found that the particle sizes provide a positive contribution to sintering and, in particular, to the color gradients between the individual powder layers.

The compressed molding to be sintered according to the invention can be obtained by stacking five or more ceramic powder layers layer by layer. The stacking of the layers may be performed, for example, in a cylindrical container to form disks. Usually, uniaxial pressing of the powder layers may be effected after each layer application. This can be done, for example, by using a press plunger, which merely causes a preliminary compaction, however. The uniaxial pressing of the layers perpendicular to the layer surface is preferably effected under a pressure of from 10 to 20 MPa, especially from 12 to 15 MPa.

In another preferred embodiment, the pressing of the stacked ceramic powder layers is performed to form a compression molding by uniaxial pressing at first, perpendicular to the layer surface, preferably to form a preliminarily compacted compressed molding having a density of below 2.8 g/cm$^3$, preferably having a density within a range of from 2.5 to 2.7 g/cm$^3$, for example, 2.65 g/cm$^3$. The uniaxial preliminary compaction may result in a better and more intimate mixing state and thus in a more uniform transition between the layers.

In another preferred embodiment, the pressing for preparing the compressed molding is performed isostatically, said isostatic pressing preferably being performed subsequently to an uniaxial preliminary compaction, to form a compressed molding having a density of below 3.4 g/cm$^3$, especially with a density of 2.80 to 3.15 g/cm$^3$, specifically with a density of 2.85 to 3.10 g/cm$^3$. Said isostatic pressing is preferably effected after all layers of the compressed molding have been stacked. Suitable pressures for said isostatic pressing are usually within a range of from 500 to 10000 bar, preferably within a range of from 800 to 8000 bar, for example, from 1000 to 7000 bar, or from 1000 to 3000 bar.

The thickness of the individual powder layers of the compressed molding may vary. In a preferred embodiment, at least two of the ceramic powder layers differ in terms of thickness. Preferably, at least two of the ceramic powder layers of the compressed molding have a difference in thickness of at least 5%. Typically, the compressed moldings may be in the form of cylindrical circular disks with diameters within a range of from 50 to 200 mm, for example, 75 to 150 mm. The total thickness of cylindrical disks may be, for example, within a range of from 8 to 40 mm, preferably from 10 to 30 mm, especially from 13 to 25 mm. The dimensions relate to the compressed molding in its unsintered state.

With respect to the color design and the subsequent processing, it has proven advantageous if at least one of the outer ceramic powder layers, preferably both outer ceramic powder layers, of the compressed molding have a larger thickness than a ceramic powder layer that is in between the outer ceramic powder layers. In particular, when the ceramic moldings prepared according to the invention are used for the preparation of dental restorations, the layer structure with at least one thicker outer layer as described above has proven advantageous, because this is a suitable structure for processing in CAD/CAM systems or other subtractive processing methods.

In a particularly preferred embodiment of the present invention, the compressed molding includes five ceramic powder layers, wherein the first powder layer comprises from 20 to 30%, preferably from 22 to 28%, the second powder layer comprises from 10 to 20%, preferably from 12 to 18%, the third powder layer comprises from 15 to 25%, preferably from 17 to 23%, the fourth powder layer comprises from 10 to 20%, preferably from 12 to 18%, and the fifth powder layer comprises from 20 to 30%, preferably from 22 to 28%, of the total thickness of the stacked powder layers, and provided that the total thickness sums up to 100%.

In another embodiment of the present invention, the sintering is effected at a temperature within a range of from 950 to 1100° C., preferably from 980 to 1050° C., to form a presintered ceramic molding (white body). Usually, the sintering is performed over a sufficient period of time for the existing binders to be removed, and for the compressed molding to be provided with sufficient strength for processing by subtractive methods. The presintered and debinded compressed moldings are referred to as "white bodies".

In one embodiment, the sintering to form the white body is performed over a period of more than 30 minutes, preferably more than 1 hour, especially more than 20 hours, or more than 50 hours, for example, from 60 to 200 hours, or from 70 to 150 hours.

In particular, for preparing ceramic dental restorations, it is appropriate that the presintered ceramic molding is processed by subtractive methods, preferably followed by final sintering in another step. When subtractive methods are applied, sinter shrinkage is usually taken into account in the calculations.

Surprisingly, it has been found that an optimum setting of the surface hardness can be achieved in a bonded layer structure using the process according to the invention. Thus, in the cutting region of a dental restoration, a lower hardness can be set as compared to the tooth neck region, for example. In a preferred embodiment of the present invention, The Vickers hardness of one outer layer is different from the Vickers hardness of the opposite outer layer. Preferably, the difference in Vickers hardness is at least 5%, more preferably at least 10%, especially at least 15%, or at least 20%, respectively based on the outer layer having the lower hardness.

Preferably, the Vickers hardness [HV2] according to DIN EN 843 of the outer layer having the lower hardness is within a range of from 45 to 60, more preferably from 50 to 59. Preferably, the Vickers hardness [HV2] according to DIN EN 843 of the outer layer having the higher hardness is above 60, and especially within a range of from 61 to 80, more preferably from 65 to 75.

Final sintering is usually performed at temperatures above 1350° C., preferably above 1400° C., especially within a range of from 1420° C. to 1600° C., or from 1450° C. to 1550° C.

The sintering time for final sintering is usually a period of more than 4 minutes, preferably more than 5 minutes, especially within a range of from 5 to 120 minutes.

The moldings according to the invention can be employed, in particular, in the dental field. They are characterized by a high edge strength in dental restorations, an excellent structure, and a high three-point bending strength. Therefore, the ceramic moldings of the present invention are preferably dental restorations, such as inlays, onlays, crowns, bridges, veneers or abutments for implants.

The present invention further relates to the use of the ceramic molding according to the invention for dental restorations, or for preparing dental restorations.

Therefore, the present invention further relates to a process for preparing a sintered molding with a color gradient for use in the preparation of dental restorations, comprising the steps of:
  a) mixing at least two, preferably at least three, different base powders for preparing five or more different ceramic powder layer mixtures;
  b) stacking the different ceramic powder layer mixtures obtained in step a) to form stacked ceramic powder layers;
  c) uniaxially pressing the ceramic powder layers perpendicular to the surface of the powder layer to form a preliminarily compacted compressed molding;
  d) isostatically pressing the preliminarily uniaxially compacted compressed molding obtained in step c); and
  e) sintering the molding obtained in step d) to form a ceramic molding, wherein the ceramic powder layers respectively have different compositions, and wherein each ceramic powder layer includes a mixture of at least two, preferably at least three, different base powders, and said base powders each have at least 80% by weight $ZrO^2$, the indicated weight being based on the total weight of the base powder.

Preferred embodiments of the process according to the invention have been explained above.

The present invention further relates to a sintered molding with a layer structure and color gradient for use in the preparation of dental restorations, wherein the molding includes at least two, preferably at least three, different ceramic powder layers, and each layer consists of at least three or four different base powders, wherein each base powder includes at least 80% by weight ceramic oxides, the indicated weights being respectively based on the total weight of the base powder.

Preferably, the ceramic powder layers include ceramic oxides as defined above. The base powders to be employed respectively correspond to the base powders as defined above.

EXAMPLES

Table 1 shows 4 base powders A to D that are employed for the compositions of the ceramic powder layers. The grain size $D_{50}$ of the base powders is within a range of from 40 to 80 µm. The inorganic components of the base powders have a particle size $D_{50}$ of from 0.2 to 0.7 µm.

The indicated weights are respectively based on the total weight of the powder composition.

TABLE 1

| Designation | Component | Proportion (% by weight) |
| --- | --- | --- |
| Base powder A | $Y_2O_3$ | 5.33 |
| | $Al_2O_3$ | 0.05 |
| | organic binder | 4 |
| | $CO_3O_4$ | 0.05 |
| | $ZrO_2$ | ad 100 |
| Base powder B | $Er_2O_3$ | 9.2 |
| | $Al_2O_3$ | 0.045 |
| | organic binder | 4 |
| | $ZrO_2$ | ad 100 |
| Base powder C | $Y_2O_3$ | 6.93 |
| | $Al_2O_3$ | 0.05 |
| | organic binder | 4 |
| | $ZrO_2$ | ad 100 |
| Base powder D | $Y_2O_3$ | 6.09 |
| | $Al_2O_3$ | 0.049 |
| | organic binder | 4 |
| | $Fe_2O_3$ | 0.2 |
| | $ZrO_2$ | ad 100 |

The arrangements of the layers set forth in the following Table 2 show the composition of each individual ceramic powder layer in the compressed molding. The compressed moldings are provided for use in the preparation of dental restorations, so that the layer compositions are designed in accordance with the position in the tooth. The compositions of the powder layers are formed from the base powders by varying the proportions to obtain an ideal color gradient. The composition of each powder layer is achieved by homogeneously mixing the base powders in the stated quantities. Subsequently, the powders are placed layer by layer into a cylindrical mold having a diameter of 100 mm, and a layer thickness of 18 mm was set. The powder layers are precompressed uniaxially under a pressure of 13 MPa perpendicular to the layer surface, and subsequently compressed isostatically under a pressure of 2000 bar.

Subsequently, debinding occurs at about 1000° C. over a period of about 100 hours. The thus obtained white bodies are milled using CAD/CAM systems into dental restorations.

These presintered and processed white bodies are subsequently subjected to final sintering at 1450° C. over a period of 120 minutes.

TABLE 2

| Powder layer | Region of restoration | Base powder C (% by weight) | Base powder D (% by weight) | Base powder B (% by weight) | Base powder A (% by weight) |
| --- | --- | --- | --- | --- | --- |
| 1 | Cutting edge | 36.90 | 51.00 | 6.10 | 6.00 |
| 2 | Dentin/Cutting edge | 30.30 | 58.00 | 6.20 | 5.50 |
| 3 | Dentin | 17.40 | 72.00 | 6.80 | 3.80 |
| 4 | Dentin/Neck | 10.60 | 76.00 | 7.40 | 6.00 |
| 5 | Neck | 3.70 | 79.00 | 8.30 | 9.00 |

In the present Example, the ceramic powder layers are arranged in such a way that layer 1 (cutting edge) comprises 25%, layer 2 (dentin/cutting edge) comprises 15%, layer 3 (dentin) comprises 20%, layer 4 (dentin/neck) comprises 15%, and layer 5 (neck) comprises 25% of the total thickness of the compressed molding.

FIG. 1 shows examples of dental restorations obtained from the exemplary ceramic molding.

The layer transitions and color transitions are fluent. The restorations exhibit an excellent edge strength and stability. Reworking and readjusting of the tooth color is not required.

The optimum structure and compositions of the layers shows a shrinkage during sintering that is substantially homogeneous throughout the layers. This is advantageous, in particular, for a perfectly fitting production of the dental restorations, since laborious reworking can be substantially avoided thereby.

Surprisingly, it has been found that the hardness of the ceramic is optimally set by the layer structure. Thus, the Vickers hardness of an exemplary disk is measured on the top side (light layer, cutting edge) and on the bottom side (dark layer, tooth neck) after firing in a kiln. As to the exemplary embodiment, the density of the white bodies and thus the Vickers hardness is always larger on the bottom side than it is on the top side.

The following Table 3 shows the determined values:

TABLE 3

| Vickers hardness [HV2] according to DIN EN 843 | |
| --- | --- |
| Mean value of Vickers hardness of cutting edge | 55.45 |
| Maximum value of Vickers hardness of cutting edge | 59.50 |
| Minimum value of Vickers hardness of cutting edge | 51.60 |
| Mean value of Vickers hardness of tooth neck | 67.76 |
| Maximum value of Vickers hardness of tooth neck | 74.70 |
| Minimum value of Vickers hardness of tooth neck | 61.20 |

The invention claimed is:

1. A sintered molding with a color gradient for use in the preparation of dental restorations, obtained by a process of:
 a) mixing at least three different base powders; for preparing five or more different ceramic powder layer mixtures;
 b) stacking of the different ceramic powder layer mixtures obtained in step a) to form stacked ceramic powder layers including at least 4 stacked ceramic powder layers,
 c) uniaxially pressing the ceramic powder layers perpendicular to the surface of the powder layer to form a preliminarily compacted compressed molding;
 d) isostatically pressing the compressed molding preliminarily uniaxially compacted in step c); and
 e) sintering the molding obtained in step d) to form a ceramic molding, wherein each ceramic powder layer includes a mixture of at least three different base powders in different amounts, at least three of the base powders include coloring metal oxides, selected from the group consisting of $Fe_2O_3$, $CO_3O_4$, and $Er_2O_3$, and said base powders each have at least 80% by weight $ZrO_2$, the indicated weight being based on the total weight of the base powder,
 each of the ceramic powder layer of the compressed molding includes $Er_2O_3$, the concentration of $Er_2O_3$ is different in each of the ceramic powder layer, each intermediate layer which is each powder layer bounded by neighboring layers that are two directly neighboring powder layers, is surrounded by one neighboring layer that has a higher concentration of $Er_2O_3$ and one neighboring layer that has a lower concentration of $Er_2O_3$ as compared to the intermediate layer,
 the compressed molding includes the ceramic powder layers, in which, proceeding from an outer ceramic powder layer, the concentration of $Er_2O_3$ increases from layer to layer,
 all powder layers include $Er_2O_3$ in an amount of from 0.01 to 1.5% by weight, based on the total weight of the powder layer.

2. The sintered molding according to claim 1, characterized in that said base powders each include at least 0.02% by weight $Al_2O_3$.

3. The sintered molding according to claim 1, characterized in that at least one of the base powders includes $Y_2O_3$ and/or $Er_2O_3$ in an amount of at least 3% by weight based on the total weight of the components of the base powder.

4. The sintered molding according to claim 1, characterized in that at least one of the base powders includes zirconia or zirconia and hafnium oxide in an amount of at least 89% by weight, respectively, based on the total weight of the components of the base powder.

5. The sintered molding according to claim 1, characterized in that each ceramic powder layer includes at least 4 base powders.

6. The sintered molding according to claim 1, characterized in that the compressed molding consists of 5 ceramic powder layers that respectively include 4 different base powders in different amounts.

7. The sintered molding according to claim 1, characterized in that the ceramic powder layers include a base powder A, which contains from 92 to 96% by weight zirconia, from 0.02 to 0.4% by weight $Al_2O_3$, from 3.5 to 10% by weight $Y_2O_3$, and from 0.02 to 0.1% by weight $Co_3O_4$, the indicated weights being respectively based on the total weight of base powder A.

8. The sintered molding according to claim 1, characterized in that the ceramic powder layers include a base powder B, which contains from 85 to 93% by weight zirconia, from 0.02 to 0.4% by weight $Al_2O_3$, and from 7.5 to 11.0% by weight $Er_2O_3$, the indicated weights being respectively based on the total weight of base powder B.

9. The sintered molding according to claim 1, characterized in that the ceramic powder layers include a base powder C, which contains from 90 to 94% by weight zirconia, from 0.02 to 0.4% by weight $Al_2O_3$, and from 5.5 to 10% by weight $Y_2O_3$, the indicated weights being respectively based on the total weight of base powder C.

10. The sintered molding according to claim 1, characterized in that the ceramic powder layers include a base powder D, which contains from 90 to 94% by weight zirconia, from 0.02 to 0.4% by weight $Al_2O_3$, from 5.5 to 10% by weight $Y_2O_3$, and 2 to 5% by weight $Fe_2O_3$, the indicated weights being respectively based on the total weight of base powder D.

11. The sintered molding according to claim 1, characterized in that the compressed molding consists of 5 ceramic powder layers, wherein the first powder layer comprises from 20 to 30%, the second powder layer comprises from 10 to 20%, the third powder layer comprises from 15 to 25%, the fourth powder layer comprises from 10 to 20%, and the fifth powder layer comprises from 20 to 30%, of the total thickness of the stacked powder layers, and provided that the total thickness sums up to 100%.

12. The sintered molding according to claim 1, characterized in that the sintered ceramic molding is presintered and processed by subtractive methods before sintering.

13. The sintered molding according to claim 1, characterized in that said uniaxial pressing is effected to form a precompacted compressed molding having a density of below 2.8 g/cm³.

14. The sintered molding according to claim 1, characterized in that said uniaxial pressing is effected under a pressure of from 10 to 20 MPa.

15. The sintered molding according to claim 1, characterized in that said isostatic pressing is effected subsequently to said uniaxial precompaction, to form a compressed molding having a density of from 2.80 to 3.15 g/cm³.

16. The sintered molding according to claim 1, characterized in that said isostatic pressing is effected under pressures of from 500 to 10000 bar.

17. The sintered molding according to claim 1, characterized in that the base powders have an average granule size $D_{50}$ of from 35 µm to 85 µm as measured by laser diffraction.

18. The sintered molding according to claim 1, characterized in that the concentration of $Fe_2O_3$ increases from layer to layer proceeding from an outer powder layer, wherein all powder layers include $Fe_2O_3$ in an amount of from 0.01 to 0.25% by weight based on the total weight of the powder layer.

19. A dental restoration made from the molding according to claim 1.

* * * * *